US006690967B2

United States Patent
Meij et al.

(10) Patent No.: US 6,690,967 B2
(45) Date of Patent: Feb. 10, 2004

(54) ELECTROCARDIOGRAM SYSTEM FOR SYNTHESIZING LEADS AND PROVIDING AN ACCURACY MEASURE

(75) Inventors: Simon H. Meij, Mijnsheerenland (NL); Stefan P. Nelwan, Rotterdam (NL)

(73) Assignee: Draeger Medical System, Inc., Danvers, MA (US)

( * ) Notice: Subject to any disclaimer, the term of this patent is extended or adjusted under 35 U.S.C. 154(b) by 0 days.

(21) Appl. No.: 09/922,170

(22) Filed: Aug. 3, 2001

(65) Prior Publication Data

US 2002/0035334 A1 Mar. 21, 2002

Related U.S. Application Data (60) Provisional application No. 60/222,806, filed on Aug. 3, 2000.

(51) Int. Cl.[7] ............................................. A61B 5/0402
(52) U.S. Cl. ....................................................... 600/509
(58) Field of Search ................................. 600/509–522

(56) References Cited

U.S. PATENT DOCUMENTS

| | | | |
|---|---|---|---|
| 4,630,204 A | 12/1986 | Mortara | 600/516 |
| 4,850,370 A | 7/1989 | Dower | 128/699 |
| 5,058,598 A | 10/1991 | Nicklas et al. | 128/699 |
| 5,318,037 A | 6/1994 | Evans et al. | 128/696 |
| 5,377,687 A | 1/1995 | Evans et al. | 128/700 |
| 5,490,515 A | 2/1996 | Mortara | 128/696 |
| 5,711,304 A | 1/1998 | Dower | 128/696 |
| 6,119,035 A | 9/2000 | Wang | 600/509 |
| 6,217,525 B1 | 4/2001 | Medema et al. | 600/508 |
| 2002/0045837 A1 | 4/2002 | Wei et al. | 600/509 |

FOREIGN PATENT DOCUMENTS

EP  1 221 299 A2  7/2002

OTHER PUBLICATIONS

Scherer J. A. et al.: "Synthesis of the 12 Lead Electrocardiogram From A 3 Lead Semi–orthogonal Subset Using Patient–Specific Linear Transformationarrays" *Proceedings of the Computers in Cardiology Meeting,* Washington Sep. 25–28, 1998 Washington IEEE Comp Soc. Press, US Vol Meeting 15, 1989.

U.S. application Ser. No. 10/354,645, Tabbara et al., filed Jan. 30, 2003.

U.S. application Ser. No. 10/286,020, Tabbara et al., filed Nov. 1, 2002.

U.S. application Ser. No. 09/844,443, Meij et al., filed Apr. 27, 2001.

*Primary Examiner*—Scott M. Getzow
(74) *Attorney, Agent, or Firm*—Jack Schwartz & Assoc.

(57) ABSTRACT

An electrocardiogram (ECG) system includes a database for containing a number of entries. Each entry contains data for synthesizing a 12 lead ECG from received ECG lead signals, and an accuracy measure of the synthesized 12 lead ECG signals. The received ECG lead signals may be missing one or more leads due to detachment of the corresponding electrode, or because the location on the patient is unavailable. The synthesized 12 lead ECG synthesizes the missing leads. Alternatively, the received 12 lead ECG may be derived from a patient in a different body position than a reference position. The synthesized 12 lead ECG translates the ECG to one for the patient in the reference body position. In addition, a synthesized lead signal may be compared to a received lead signal to detect anomalous signals.

33 Claims, 6 Drawing Sheets

Synthesis

Fig. 1 - Analysis

Fig. 2 – Analysis flowchart a)

| S | | M[V1] | | | | | | | | I |
|---|---|---|---|---|---|---|---|---|---|---|
| SI | = | 1 | 0 | 0 | 0 | 0 | 0 | 0 | 0 | I |
| SII | | 0 | 1 | 0 | 0 | 0 | 0 | 0 | 0 | II |
| SV1 | | CI(V1) | CII(V1) | 0 | CV2(V1) | CV3(V1) | CV4(V1) | CV5(V1) | CV6(V1) | V1 |
| SV2 | | 0 | 0 | 0 | 1 | 0 | 0 | 0 | 0 | V2 |
| SV3 | | 0 | 0 | 0 | 0 | 1 | 0 | 0 | 0 | V3 |
| SV4 | | 0 | 0 | 0 | 0 | 0 | 1 | 0 | 0 | V4 |
| SV5 | | 0 | 0 | 0 | 0 | 0 | 0 | 1 | 0 | V5 |
| SV6 | | 0 | 0 | 0 | 0 | 0 | 0 | 0 | 1 | V6 | b)

| S | | M[V1,V3] | | | | | | | | I |
|---|---|---|---|---|---|---|---|---|---|---|
| SI | = | 1 | 0 | 0 | 0 | 0 | 0 | 0 | 0 | I |
| SII | | 0 | 1 | 0 | 0 | 0 | 0 | 0 | 0 | II |
| SV1 | | CI(V1) | CII(V1) | 0 | CV2(V1) | 0 | CV4(V1) | CV5(V1) | CV6(V1) | V1 |
| SV2 | | 0 | 0 | 0 | 1 | 0 | 0 | 0 | 0 | V2 |
| SV3 | | CI(V3) | CII(V3) | 0 | CV2(V3) | 0 | CV4(V3) | CV5(V3) | CV6(V3) | V3 |
| SV4 | | 0 | 0 | 0 | 0 | 0 | 1 | 0 | 0 | V4 |
| SV5 | | 0 | 0 | 0 | 0 | 0 | 0 | 1 | 0 | V5 |
| SV6 | | 0 | 0 | 0 | 0 | 0 | 0 | 0 | 1 | V6 |

Fig. 3 – Matrix math

Fig. 4 - Synthesis

Fig. 5 – BPC flowchart

Fig. 6 – BPC synthesis flowchart

ELECTROCARDIOGRAM SYSTEM FOR SYNTHESIZING LEADS AND PROVIDING AN ACCURACY MEASURE

The present application is a non-provisional application based on a provisional application, Ser. No. 60/222,806, filed Aug. 3, 2000, entitled "Signal Processing Apparatus, Monitoring Method, User Interface [sic], and Analysis System for Synthesizing an Electrocardiogram."

FIELD OF THE INVENTION

The present invention relates to electrocardiogram (ECG) systems, and in particular to ECG systems which can provide synthesized signals corresponding to signals generated from electrodes which provide the actual ECG signals.

BACKGROUND OF THE INVENTION

ECG systems are well known, and provide information about the physiological status of a patient's heart to a physician. More specifically, so called 12 lead ECG systems exist which provide twelve waveforms, called leads, to the physician. To provide such a 12 lead ECG, ten electrodes are placed on the patient's body, and the signals from these electrodes are processed to provide the twelve leads, all in a known manner. These ten electrodes include four electrodes which provide signals processed to generate six of what are known as limb leads, and six electrodes which provide signals processed to provide six of what are known as precordial or chest leads.

In some cases, signals from all ten electrodes, necessary for proper derivation of a 12 lead ECG, are not available. For example, sometimes, electrodes work loose from, or slip on, a patient's body and produce a null signal, or produce signals which are otherwise degraded to the point of being unusable. Furthermore, the location on the patient's body at which one or more of the electrodes should be placed may be unavailable due to injury or surgery. As another example, in non-critical monitoring or telemetry conditions, modules providing only five or six electrodes are provided, both for patient comfort and to minimize the signal processing required.

In other cases, it may be desirable to place an electrode at a location on the body different from the normally used locations. For example, it may be desired to monitor the right side of the heart, or further around the left side.

In any case, electrodes are sometimes placed in incorrect locations, or two electrodes are reversed. Also electrodes may provide anomalous signals. For example, if an electrode has worked loose from, or slipped on, a patient, the signal from that electrode is not accurate. Alternatively, if a patient moves (e.g. rolls on his side, or sits up), the signal from all the electrodes, even if accurate, may provide anomalous results after analysis due to the patient movement. It is desirable under all the conditions described above to still provide the signals needed to generate the 12 lead ECG.

It is known that the signals representing the respective lead signals contain mutually redundant information. It is also known that, should one electrode be missing or malfunctioning, an appropriate combination of signals from the other electrodes and/or the other leads, which are available and functional, can be used to generate a synthesized signal which closely approximates the lead signal derived from the missing or malfunctioning electrode. To apply this technique, at least some portion of a full 12 lead ECG is recorded, during an analysis phase. The recorded signals are then processed to generate a function, which may be applied to the lead signals which are available, to synthesize a lead signal which approximates the lead signal which is missing or distorted beyond use. During a synthesis phase, this function is then applied to the available ECG lead signals. Using this technique, a missing lead may be synthesized.

In U.S. Pat. No. 5,058,598, issued Oct. 22, 1991 to Nicklas et al., a system is disclosed for synthesizing a desired precordial lead from what is termed a set of base leads. First, in an analysis phase, a set of ECG lead signals, including at least the set of base leads (in Nicklas et al, the base leads are leads I, II, and V2), and the precordial lead signal (other than V2) which is desired to be synthesized, is processed to generate coefficients for a linear equation. Then, in a synthesis phase, signals representing only the base leads are received, and the values of those base leads are substituted into the linear equation to derive values which represent the desired synthesized precordial lead signal. Nicklas et al. also discloses partitioning the ECG complex into segments (e.g. QRS, ST, etc.), and processing each segment separately to generate respective sets of coefficients for a separate linear equation corresponding to each segment. In this case, during the synthesis phase, values for each segment from the base leads are substituted into the appropriate linear equation, to derive values which represent the desired synthesized precordial lead signal in that segment.

In U.S. Pat. No. 5,490,515, issued Feb. 13, 1996 to Mortara, a system is disclosed for synthesizing a single specified lead from a set of eight lead signals. In the analysis phase, the set of eight lead signals, derived from respective electrodes, is received by the system and a coefficient table, having entries representing coefficients of a set of linear equations, is generated. In the synthesis phase, the coefficient table is then used to synthesize a selected one of the eight lead signals, based on the values of the other seven lead signals. Mortara also discloses simultaneously synthesizing more than one missing lead.

In neither of these systems is any indication of the accuracy of the synthesized signal provided to the operator. In addition, in neither of these systems is any information provided to the operator to alert the operator to anomalous signals, nor to assist in preparation for the ECG or in interpreting the displayed 12 ECG lead waveforms.

It is desirable to determine the accuracy of the synthesized signal relative to other potential synthesized signals, and to provide that information to the operator. It is further desirable to provide information to the operator to alert the operator to anomalies, and to assist in the preparation for the ECG and the interpretation of the results. In some cases, such as telemetered ECGs, it is further desirable to monitor patients with a minimum number of electrodes, while producing a full 12 lead ECG and maintaining a desired level of accuracy.

BRIEF SUMMARY OF THE INVENTION

In accordance with principles of the present invention, an electrocardiogram (ECG) system provides a set of ECG lead signals. The system includes a source of a subset of ECG lead signals. A synthesizer, coupled to the ECG lead signal source, generates a set of synthesized ECG lead signals from the subset of ECG lead signals. Data is also generated representing the accuracy of the set of synthesized ECG lead signals.

DETAILED DESCRIPTION OF THE INVENTION

Figure 1:
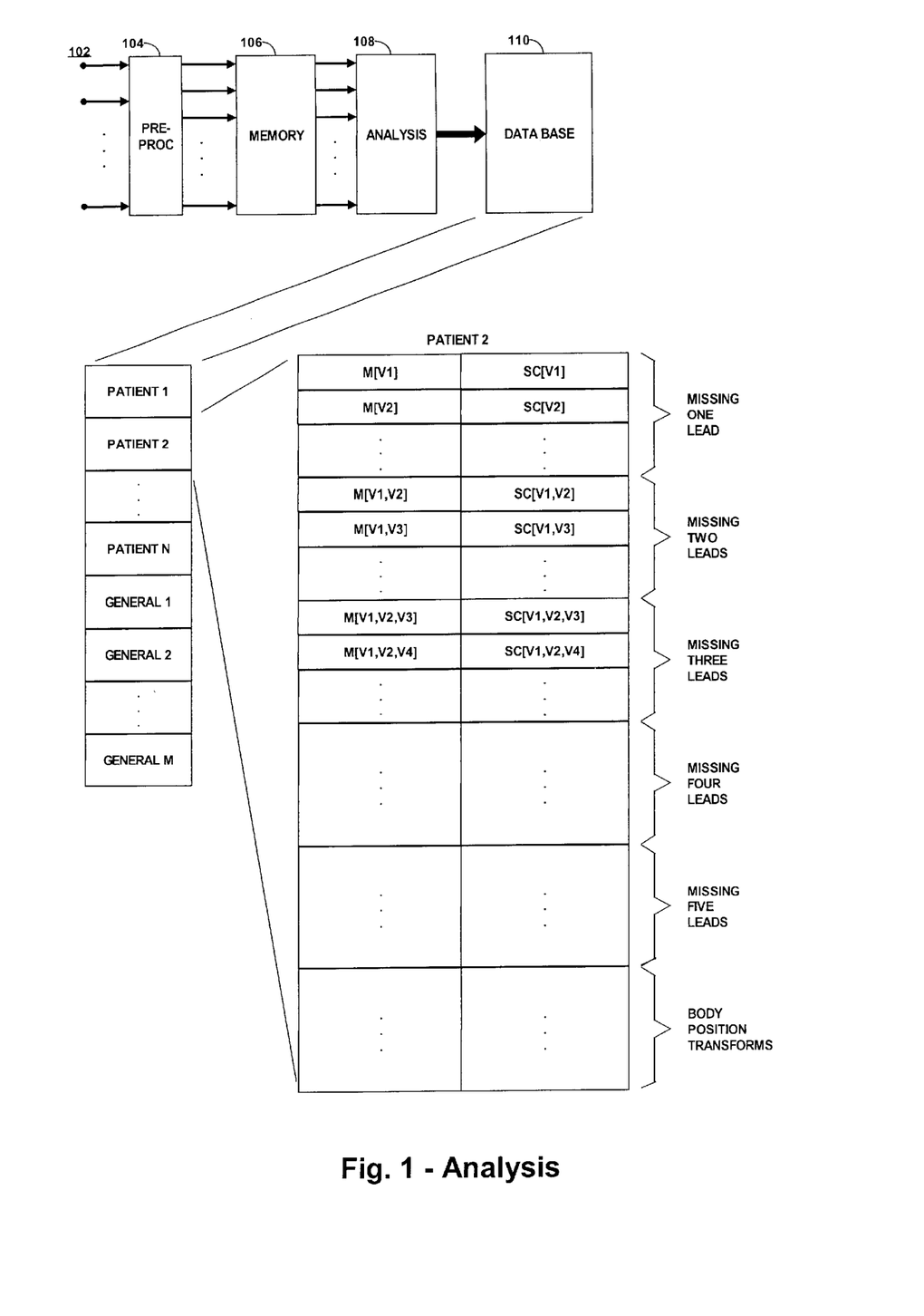
FIG. 1 is a diagram in block form with the database block also shown in memory layout form, illustrating a portion of an ECG system according to principles of the present invention.

FIG. 1 is a diagram in block form with the database block also shown in memory layout form, illustrating a portion of an ECG system according to principles of the present invention. In FIG. 1, a plurality 102 of electrodes are intended to be attached to respective locations on a patient's body. The plurality 102 of electrodes are coupled to respective input terminals of a preprocessor 104. Respective output terminals of the preprocessor 104 are coupled to corresponding input terminals of a memory 106. Respective output terminals of the memory 106 are coupled to corresponding input terminals of an analysis circuit 108. An output terminal of the analysis circuit 108 is coupled to an input terminal of a database 110.

In operation, the plurality 102 of electrodes are ECG electrodes which are intended to be attached to predetermined locations on a patient. In the illustrated embodiment, 10 electrodes are provided. The preprocessor 104 processes the signals from the 10 electrodes to generate signals representing a 12 lead ECG at respective output terminals. More specifically, signals from the four limb lead electrodes are processed to provide limb lead signals I and II. From limb lead signals I and II, the remaining limb lead signals III, aVR, aVL and aVF, may be mathematically derived. In the illustrated embodiment, the derivation of those other limb lead signals is not germane to the present invention and they are not discussed in the remainder of this application. The other six electrodes are processed separately to provide corresponding precordial lead signals (V1, V2, V3, V4, V5, V6). Thus, signals representing eight lead signals (I, II, V1, V2, V3, V4, V5, V6) are generated by the preprocessor 104 in a known manner and are further processed in the manner described below.

In the illustrated embodiment this preprocessing further includes analog-to-digital conversion. The eight lead signals, therefore, are in multibit digital form. The preprocessor 104 may further provide processing to identify characteristics of each ECG complex and to time align and aggregate (e.g. average, median filter, etc.) some number of successive ECG complexes for each lead, all in a known manner. Digital data representing the eight, possibly aggregated, ECG lead complexes is stored, in a known manner, in respective locations in the memory 106.

Figure 2:
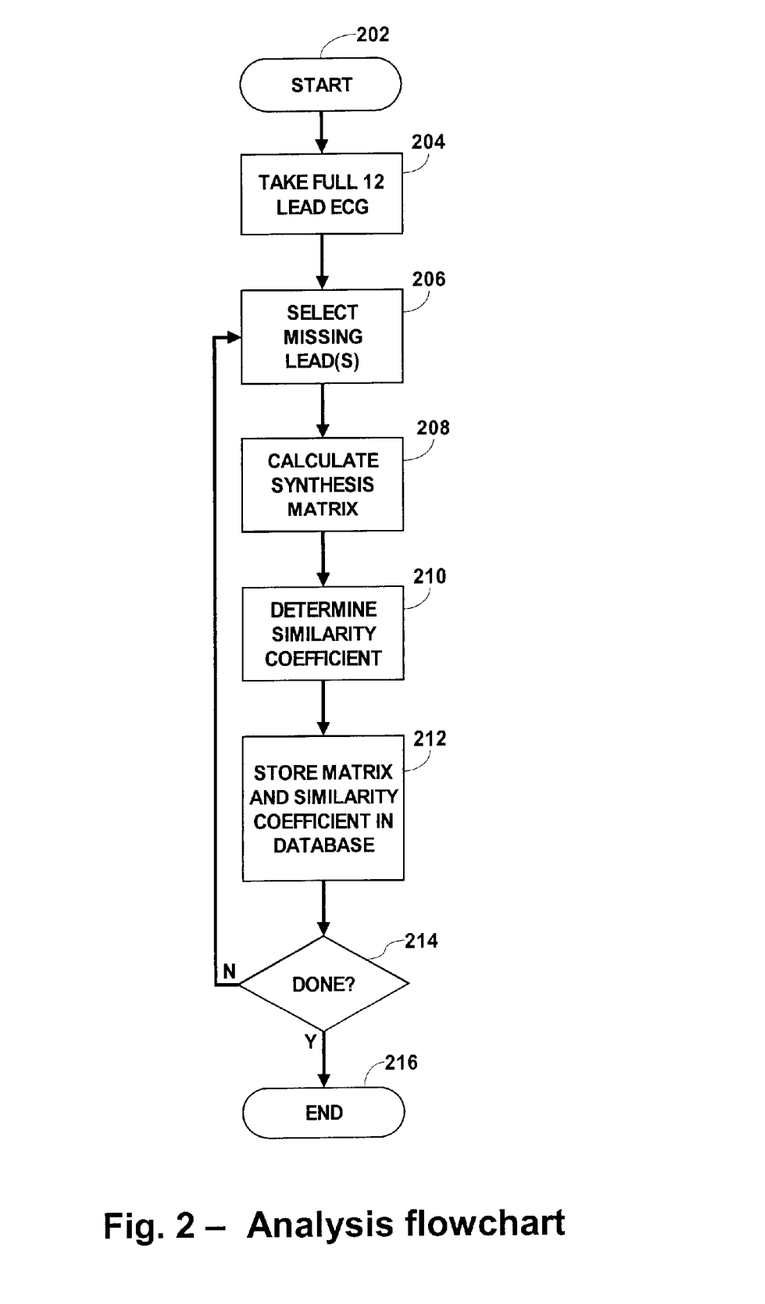
FIG. 2 is a flowchart useful in understanding the operation of the system illustrated in FIG. 1.

FIG. 2 is a flowchart useful in understanding the analysis phase operation of the analysis system illustrated in FIG. 1. The operation starts in block 202. In block 204 a full 12 lead ECG is taken and the result, as described above, is multibit digital data representing eight respective ECG lead complexes (I, II, V1, V2, V3, V4, V5, V6), possibly aggregated. The data representing these eight lead complexes are stored in respective locations in the memory 106, all in a known manner.

The analysis circuit 108 retrieves data, in a known manner, from the locations in the memory 106 corresponding to the eight lead complexes. The analysis circuit 108 then analyzes the retrieved data. In general, every possible combination of one or more of the leads is treated as if it were missing or otherwise unusable. Then, for each such combination, the other remaining lead complexes, treated as if they remain available, are compared to the missing lead complex or complexes, and a function of the available lead complexes is calculated which will most accurately synthesize the one or more missing leads from the available leads. A measure of the accuracy of the synthesis is also determined and both the calculated function and the determined accuracy measure are stored in the database 110. The processing applied to each such combination is illustrated in FIG. 2 and described in more detail below.

In block 206 a subset of leads, consisting in the first place of one of the eight leads, is selected as the missing lead. For the purposes of the following description, the selected lead is the precordial lead V1. In block 208, the stored lead complex data representing the selected lead V1 is compared to the stored lead data representing the other seven lead complexes (I, II, V2, V3, V4, V5 and V6) to calculate a function of those other seven lead complexes (I, II, V2, V3, V4, V5 and V6) which will most closely approximate the selected lead complex (V1).

In the illustrated embodiment, a synthesized lead complex SV1, approximating the selected lead complex V1, is synthesized by a linear combination of the other seven lead complexes (I, II, V2, V3, V4, V5 and V6). That synthesis is represented by a set of coefficients {CI(V1), CII(V1), CV2 (V1), CV3(V1), CV4(V1), CV5(V1) and CV6 (V1)}. The notation Cx(y) is intended to represent the coefficient C to be applied to the $x^{th}$ available lead complex to synthesize the missing $y^{th}$ lead complex. That is, this set of coefficients represents the proportion of the other seven lead complexes (I, II, V2, V3, V4, V5 and V6), respectively, in the linear combination representing the synthesized lead complex SV1 most closely approximating the missing lead complex V1. In the illustrated embodiment, the coefficients are calculated using a least squares linear regression with a zero intercept vector, in a known manner. One skilled in the art will understand that any form of combination, such as polynomial or trigonometric, could also be used.

Figure 3:
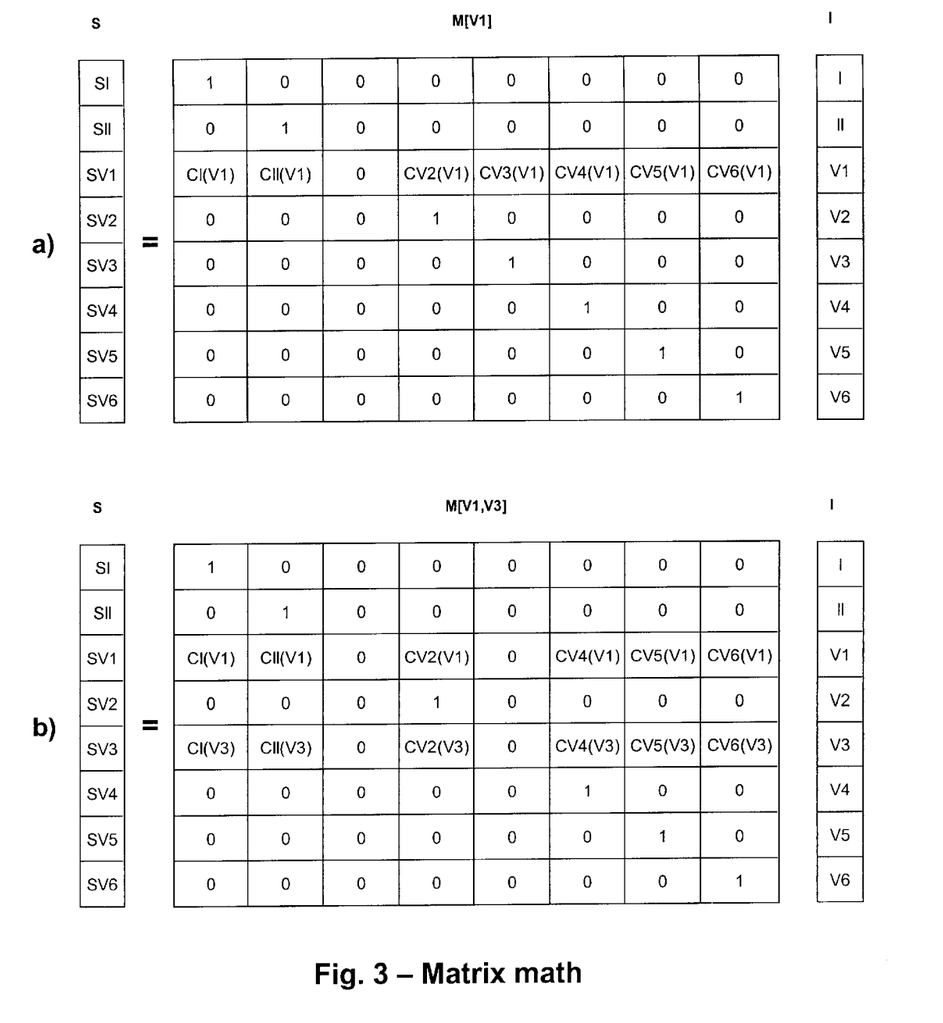
FIG. 3 is a diagram illustrating matrix calculations which are useful in understanding the operation of the present invention.

The calculation in block 208 produces a synthesis matrix M. FIG. 3 is a diagram illustrating matrix calculations which are useful in understanding the operation of the present invention. In FIG. 3a, a matrix M[V1] illustrates a matrix which is produced when the selected lead is lead V1. The notation M[z] is intended to represent the synthesis matrix M for synthesizing the synthesized vector S from an input vector I missing the set {z} of ECG lead complexes. An input vector I contains elements representing data points from the eight lead complexes (I, II, V1, V2, V3, V4, V5, V6). The matrix M[V1] has as its basis an identity matrix. However, the row corresponding to the synthesized lead complex SV1 (e.g. the third row from the top) is replaced by the set of coefficients {CI(V1), CII(V1), 0, CV2(V1), CV3 (V1), CV4(V1), CV5(V1) and CV6(V1)} calculated in block 208 by the analysis circuit 108. The column corresponding to the selected lead complex V1 (e.g. the third column from the left) is set to zero, so that the selected lead complex V1 makes no contribution to the combination forming the synthesized selected lead complex SV1.

One skilled in the art will understand that when the synthesis matrix M[V1] is multiplied by the input vector I, the result is a synthesized vector S. The synthesized vector S contains elements representing synthesized data points for the eight synthesized lead complexes (SI, SII, SV1, SV2, SV3, SV4, SV5, SV6), in which the synthesized lead complex SV1 for the selected lead is synthesized from the other seven leads (I, II, V2, V3, V4, V5, V6) while the remaining leads (SI, SII, SV2, SV3, SV4, SV5, SV6) are equal to the corresponding elements in the input vector I.

In block 210 a similarity coefficient SC is determined in the following manner. When the matrix M[V1] has been calculated in block 208, it is used to generate eight synthesized lead complexes (SI, SII, SV1, SV2, SV3, SV4, SV5, SV6). Then the synthesized lead complexes (SI, SII, SV1, SV2, SV3, SV4, SV5, SV6) are compared to the actual leads complexes (I, II, V1, V2, V3, V4, V5, V6) stored in the memory 106 to calculate a similarity coefficient SC. This is designated in FIG. 1 as SC[V1] to indicate that it is the similarity coefficient SC for the selected lead V1. In the illustrated embodiment, this coefficient SC[V1] is calculated from the differences between the root mean square (RMS) values of the synthesized lead complex data (SI, SII, SV1, SV2, SV3, SV4, SV5, SV6) and the stored actual lead complex data (I, II, V1, V2, V3, V4, V5, V6). More specifically, the synthesis coefficient SC is calculated as.

$$SC = 1 - \frac{RMS_{source} - RMS_{error}}{RMS_{source}}.$$

Alternatively, the known Pearson's correlation technique may be used to generate a similarity coefficient SC. One skilled in the art will understand, however, that any technique of rating the similarity of the synthesized lead complexes to the actual lead complexes may be used.

In step 212, the calculated matrix M[V1] and the corresponding similarity coefficient SC[V1] are stored in the database 110 in a known manner. The database 110 is maintained on a non-volatile storage device. For example, the database may be located on a disk drive system in a central location accessible by a hospital network, in a known manner. The specific configuration of the storage device and database 110 is not germane to the invention, provided it is accessible by the ECG system.

One skilled in the art will understand from FIG. 1 that the database 110 contains a plurality of entries respectively corresponding to different patients and to different general populations. This will be described in more detail below. Each patient and general population entry contains a sequence of synthesis entries corresponding to different sets of selected (missing) lead complexes, derived as described above. In FIG. 1, the entry for patient 2 is illustrated. The patient 2 entry in turn contains a first synthesis entry into which the matrix M[V1] and the similarity coefficient SC[V1] is stored. Other data not germane to the present invention may also be stored in the patient entry and/or the patient entry's synthesis entries.

In block 214, if all the synthesis entries have been filled, then the process ends in block 216. Otherwise processing returns to block 206 where another subset of leads is selected and treated as missing. In the illustrated embodiment, all subsets consisting of a single missing lead are processed, followed by all subsets consisting of two missing leads, all subsets consisting of three missing leads, and so forth. One skilled in the art will understand that the order in which the subsets are determined and processed is not germane to the present invention.

More specifically, in the illustrated embodiment, the precordial lead V2 is selected next and the processing described above performed again. In this case, referring again to FIG. 1, the results of this processing, M[V2] and SC[V2], are stored in the second synthesis entry in the patient 2 entry.

This continues for all of the remaining subsets of a single missing lead. Then all sets of two simultaneously missing leads are processed. For example, leads V1 and V2 are simultaneously selected and treated as missing and the same processing described above performed and the results, synthesis matrix M[V1,V2] and similarity coefficient SC[V1, V2], are stored in the appropriate patient 2 synthesis entry. Then the next set of two missing leads, V1 and V3 are simultaneously selected and treated as missing and the same processing performed.

FIG. 3b illustrates a matrix M[V1,V3] which is calculated in response to the simultaneous selection of leads V1 and V3 as missing. As before, the matrix M[V1,V3] has as its basis the identity matrix. But in this case the row corresponding to the synthesized lead SV1 is replaced with coefficients CI(V1), CII(V1), 0, CV2(V1), 0, CV4(V1) CV5(V1) and CV6(V1) and the row corresponding to the synthesized lead SV3 is replaced with coefficients CI(V3), CII(V3), 0, CV2 (V3), 0, CV4(V3), CV5(V3) and CV6(V3). At the same time, the columns corresponding to the selected lead complexes V1 and V3 are replaced with zeroes to ensure that input signals from those lead complexes do not contribute to the synthesized lead signals. Again, a similarity coefficient SC[V1, V3] is determined and both the matrix M[V1, V3] and the similarity coefficient SC[V1,V3] are stored in the appropriate synthesis entry in the patient 2 entry. This continues for all sets of two missing leads, followed by all combinations of three missing leads and so forth until the patient 2 entry is completed and the process ends in block 216 (of FIG. 2).

Figure 4:
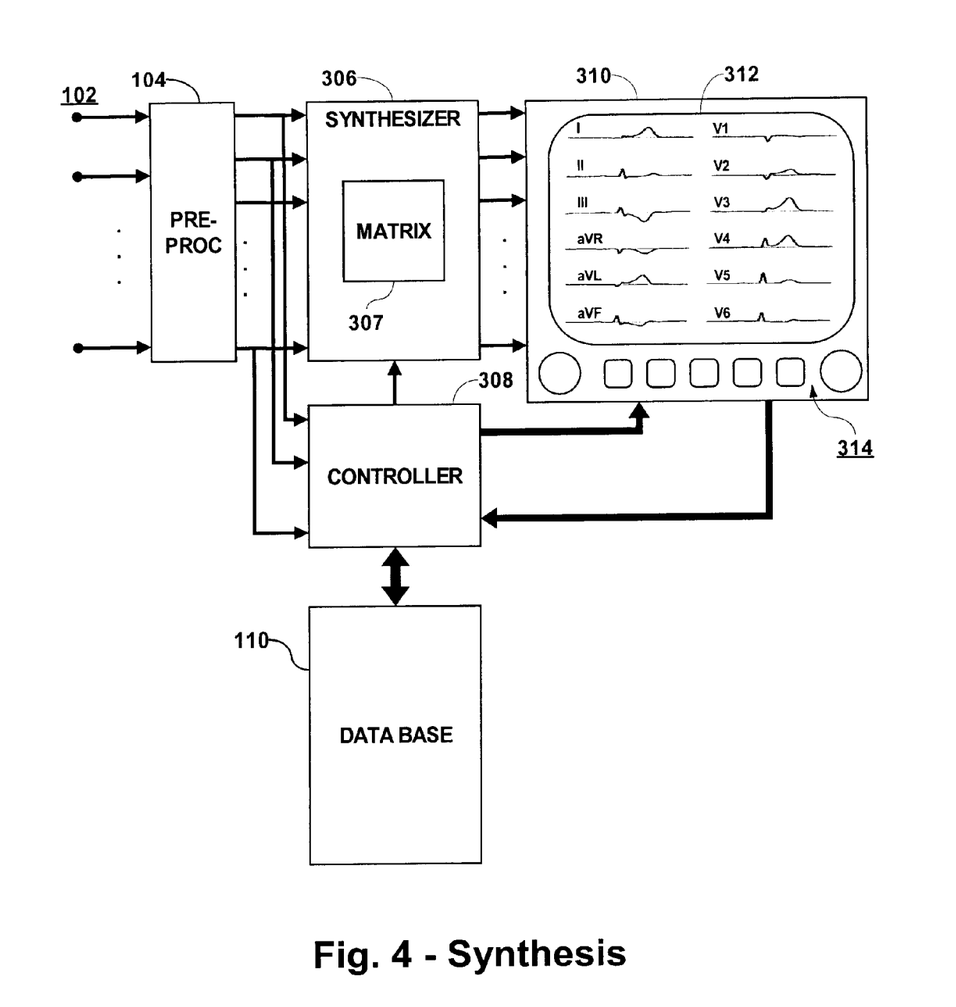
FIG. 4 is a block diagram illustrating a different portion of a system according to principles of the present invention.

As was disclosed in Nicklas et al. it is possible to partition each of the eight lead complexes stored in the memory 108 into segments, and perform the calculations described above on each segment independently. In the present invention, this would result in a plurality of matrices, one for each segment, stored in each synthesis entry in the patient 2 entry. When the missing lead(s) is synthesized from the available leads, the appropriate matrix is used depending on which segment is currently being synthesized, all as disclosed in Nicklas et al. FIG. 4 is a block diagram illustrating a synthesis portion of a system according to principles of the present invention. In FIG. 4, those elements which are the same as those illustrated in FIG. 1 are designated by the same reference number and are not described in detail below. In FIG. 4, the respective output terminals of the preprocessor 104 are coupled to corresponding input terminals of a synthesizer 306 and a controller 308. Respective output terminals of the synthesizer 306 are coupled to corresponding data input terminals of a display device 310. A synthesizer control output terminal of the controller 308 is coupled to a control input terminal of the synthesizer 306, and a display device control output terminal of the controller 308 is coupled to a control input terminal of the display device 310. The display device 310 includes a display screen 312 and a set of user controls 314. These user controls 314 may include, among other controls, knobs, illustrated as circles, and buttons, illustrated as rounded squares. A user control output terminal of the display device 310 is coupled to a user control input terminal of the controller 308. A bidirectional terminal of the controller 308 is coupled to a corresponding terminal of the database 110.

As illustrated in FIG. 4, the display device 310 can display the 12 lead ECG waveforms from the synthesizer 306 on the display screen 312 in the usual manner for ECG waveforms. In addition, the controller 308 can respond to user input from the user controls 314 on the display device 310, and can condition the display device 310 to display information on the display screen 312. The controller 308 can also control the operation of the synthesizer 306 in response to the lead signals from the preprocessor 104, in a manner to be described in detail below. The synthesizer 306 in turn performs the matrix multiplication illustrated in FIG. 3 on the lead signals received from the preprocessor 104 to generate the lead signals, possibly including synthesized lead signals, for the display device 310.

In general operation, the plurality of electrodes 102 are attached to predetermined locations on a patient by an operator. The operator then manipulates the user controls 314 to enter information concerning the monitoring desired, including, e.g. the identification of the patient. The controller 308 then conditions the synthesizer 306 to operate in a normal mode. The preprocessor 104 provides the eight lead signals to the synthesizer 306. In the normal mode, all of the plurality 102 of electrodes are operational, and all lead signals from the preprocessor 104 are accurate. The controller 308 conditions the synthesizer 306 to pass the input lead signals through to the output without change. This may be done by placing an identity matrix in the matrix 307 of the synthesizer 306. The synthesizer 306 performs the matrix multiplication illustrated in FIG. 3 using the identity matrix to transfer the received 12 lead signals to the display device 310. The display device 310, in turn, displays the 12 lead ECG waveforms from the synthesizer 306 on the display screen 312 all in a normal manner. In this mode of operation, the similarity coefficient has its maximum value.

As described above, however, it is possible for one or more electrodes to detach from or become loose on the patient. This may be detected automatically by the controller 308 by any of a number of known techniques. For example, if no pulse component is detected in a lead signal, then that lead signal may be identified as inoperative.

In such a case, the controller 308 retrieves the entry from the database 110 for the current patient, e.g. patient 2 (as illustrated in FIG. 1), and from that entry retrieves the matrix M appropriate for synthesizing the lead or leads which have been identified as inoperative. For example, if lead V1 is identified as inoperative, then the matrix M[V1] is retrieved from the patient 2 entry of the database 110. The controller 308 then inserts that matrix M into the matrix 307 in the synthesizer 306. The synthesizer 306 performs the matrix multiplication described above with reference to FIG. 3, to provide a synthesized signal for the lead or leads which are inoperative. The display device 310 continues to display the 12 lead waveforms received from the synthesizer 306, including the synthesized lead waveform or waveforms.

The controller 308 may further condition the display device 310 to display an indication on the display screen 312 to alert the operator that one or more of the displayed leads are being synthesized. This indication may include highlighting the synthesized lead waveform(s) or the background of the synthesized lead waveform(s), in some fashion, such as varying the intensity or color of the synthesized lead waveform(s) relative to the other lead waveforms; or placing an indicative symbol in the vicinity of the synthesized waveform(s); or displaying a textual identification of the synthesized waveform(s) on the display screen 312. In addition, the controller 308 may retrieve the corresponding similarity coefficient SC from the database 110 and display that on the display screen 312 as an indication of the expected accuracy of the displayed waveforms.

The synthesis technique described above may also be used to identify anomalous lead signals. The controller 308 successively retrieves from the database 110 the matrices for the current patient for synthesizing a single missing lead. That is, first the matrix M[I] is retrieved, then the matrix M[II], then the matrix M[V1] and so forth. As each matrix is retrieved, the controller 308 inserts the retrieved matrix M into the matrix 307 in the synthesizer 306. The synthesizer 306 performs the matrix multiplication described above to provide a synthesized ECG lead signal for the corresponding ECG lead signal. This synthesized ECG lead signal is compared to the corresponding lead signal from the preprocessor 104. The results of this comparison can be used to identify anomalous lead signals from the pre-processor 104. That is, if the synthesized ECG lead signal is not substantially the same as the corresponding ECG lead signal, this indicates an anomalous ECG lead signal.

For example, the synthesized ECG lead signal may be correlated against the corresponding ECG lead signal. If there is a high level of correlation between the lead signal from the pre-processor 104 and the corresponding synthesized signal from the synthesizer 306, then the lead signal from the pre-processor 104 is considered to be accurate. If, however, there is not a high level of correlation, then the lead signal from the pre-processor 104 is considered to be inoperative. In this case, the processing described above is performed to display the synthesized lead signal on the display screen 312 of the display device 310. This process may be repeated at intervals to maintain a check on the accuracy on the lead signals from the pre-processor 104.

As another example, it is commonly realized that locations of electrodes on the body of a patient may be easily reversed by the operator of the ECG monitor. For example, it is relatively common for the locations of the RA and LA electrodes to be reversed on the patient. This leads to an inverted I lead signal. By performing the procedure described above, a synthesized I lead may be compared to the I lead signal from the pre-processor 104. A strong positive correlation indicates that the RA and LA electrodes are correctly placed. A strong negative correlation, on the other hand, indicates that the locations of the RA and LA electrodes have been reversed. In response to indication, the operator may be alerted to properly locate the RA and LA electrodes by display of a message on the display screen 312 of the display device 310 and/or an audible alert.

Also as described above, all the desired locations on the body of the patient may not be available due to surgery or injury. In this case, the operator can manipulate the user controls 314 to provide an indication of the sites which are unavailable to the controller 308. The controller 308 will then generate a list of electrode configurations for the available locations, and access the data in the database 110 entry associated with this patient to retrieve the similarity coefficients SC associated with each of the electrode configurations. The configuration with the highest similarity configuration SC, i.e. generating the most accurate 12 lead ECG waveform synthesis, is then displayed on the display screen 312 of the display device 310. This display may be textual, or it may be graphical providing a drawing of the patient with the specified electrode locations displayed on that drawing. The controller 308 retrieves the matrix M associated with that configuration and places it in the matrix 307 in the synthesizer 306. In accordance with the displayed information, the operator then applies the electrodes in this desired configuration. Then the display of the 12 lead ECG waveforms can proceed as described above, optionally including specially highlighting the synthesized lead waveforms and displaying the similarity coefficient.

Alternatively, the complete list of available electrode configurations along with their similarity coefficients may be displayed on the display screen 312 of the display device 310. The operator can then select one of the available configurations based not only on the similarity coefficients but possibly also on other clinical considerations. The operator then manipulates the user controls 314 to indicate which of the configurations has been selected, and applies the electrodes in that configuration. The controller 308 retrieves the appropriate matrix M from the database 110 and supplies it to the matrix 307 in the synthesizer 306. The controller 308 then conditions the synthesizer 306 to synthesize the 12 lead ECG waveforms for that configuration, as described above.

By either automatically specifying the electrode configuration with the highest similarity coefficient, or by providing a list of electrode configurations with an associated similarity coefficient to the operator for selection, it is assured that an electrode configuration producing 12 lead ECG waveforms with the maximum accuracy, or the maximum accuracy given the existing clinical considerations, will be used.

It is sometimes desired to use a non-standard electrode configuration. For example, a physician may desire data related to the right side of the heart, or further around the left side of the heart. The former requires one or more electrodes placed at locations to the right of the heart, and the latter at locations further to the left of the heart. There are predetermined such locations known as V1R, V2R, V3R, V4R, V5R and V6R on the right side of the chest and V7, V8 and V9 around the left side of the patient. Prior systems required either extra electrodes and circuitry to process signals and display the waveforms from them, or that electrode(s) be removed from the standard locations V1, V2, V3, V4, V5 and V6 to be placed at the other location(s) V7, V8, V9, V1R, V2R, V3R, V4R, V5R and V6R. Moving a lead from a standard location meant losing the lead signal generated by that electrode.

In the system illustrated in FIG. 4, the operator manipulates the user controls 314 on the display device 310 to indicate that it is desired to move one or more of the electrodes from their standard locations to another location. In response, the controller 308 retrieves the entry in the database 110 corresponding to the patient, and retrieves all of the similarity coefficients SC for the configurations missing the number of leads desired to be moved. That is, if two leads are desired to be moved, then the controller 308 retrieves the similarity coefficients SC for all of the configurations missing two leads. The controller 308 then automatically selects the configuration having the highest similarity coefficient SC from among those retrieved, and displays information on the display screen 312 of the display device 310 specifying the electrode configuration corresponding to that similarity coefficient SC. The operator places the appropriate electrodes at the specified standard locations on the patient, and then places the remaining leads at the other non-standard desired locations.

The controller 308 then retrieves the matrix M corresponding to the specified electrode configuration from the database 110 and supplies it to the matrix 307 in the synthesizer 308. The synthesizer 306 then synthesizes the standard 12 lead ECG waveforms from the available leads in the standard locations in the manner described above. The controller 308 may further condition the display device 310 to simultaneously display the 12 lead ECG waveforms and the lead waveforms from the other locations (e.g. from the right side of the chest) on the display screen 312, in a known manner. As before, the synthesized waveforms may be specially identified on the display screen and/or the similarity coefficient displayed.

Also as before, alternatively, a list of possible electrode configurations with their respective similarity coefficients, may be displayed on the display screen 312 of the display device 310, from which the operator selects one based on the similarity coefficients and other clinical considerations. The operator manipulates the user controls to select one of the configurations and the controller 308 conditions the system to operate in that configuration as described above. Again, as before, use of the similarity coefficients permits synthesis of the standard 12 lead ECG waveforms having the maximum accuracy, or the maximum accuracy based on existing clinical considerations.

In some situations, the use of the full set of 10 electrodes to produce the full 12 lead ECG is not desirable, for example, if a patient is being transported from one location to another, or if the ECG is being monitored by telemetry. In these situations, it is desired to use the minimum number of electrodes for patient comfort, while still maintaining a desired level of accuracy in the ECG. Alternatively, in some situations, the ECG monitor is miniaturized and does not include the full 10 electrodes.

Under these situations, the controller 308 retrieves the patient entry from the database 110. The similarity coefficients SC for all the synthesis entries corresponding to one missing lead are compared, and the entry with the largest similarity coefficient is selected. Similarly the similarity coefficients for all the synthesis entries corresponding to two missing leads are compared and the entry with the largest similarity coefficient is selected. This is repeated for each possible number (three, four, etc.) of missing leads. Then the list of selected entries, including the electrode configuration and the similarity coefficient, is displayed on the display screen 312 of the display device 310. The operator then selects the entry which satisfies the minimum accuracy desired using the user controls 314, and attaches the electrodes to the patient according to the configuration represented by that entry. The controller 308 conditions the system to synthesize the 12 lead ECG from the selected electrode configuration. In this manner, the highest accuracy for the number of electrodes selected is guaranteed, while minimizing to the extent possible the number of electrodes necessary, thus, minimizing patient discomfort.

In the preceding description, it was assumed that a full 12 lead ECG for the patient was previously available to be analyzed. This may not always be the case. When an ECG for a patient is not previously available, of course, there can be no entry in the database 110 for that patient. Referring again to FIG. 1, 12 lead ECG data from a large population may be analyzed by the analysis circuit 108 as a group, in the manner illustrated in FIG. 2. In this case, the eight lead complexes assembled in the memory 106 by block 204 will be generated as the aggregation of all the available eight lead ECG complexes for all the people in the population. These general-population lead complexes will be analyzed in the manner illustrated in FIG. 2 above to produce a set of general-population matrices M and corresponding similarity coefficients SC. This set of matrices M and similarity coefficients SC will be stored in a general population entry in the database 110, illustrated in FIG. 1 as an entry labeled GENERAL 1. The entry GENERAL 1 has exactly the same data structure as that illustrated for Patient 2. The data in the GENERAL 1 entry is based on the aggregated 12 lead complexes for the entire population, however.

If a patient does not have an entry in the database 110, then the general population entry GENERAL 1 is retrieved, and the data in that entry used in exactly the same manner as described above for any of the situations described above: e.g. detecting anomalous lead signals, synthesizing detached electrodes, or synthesizing leads for electrodes whose locations are unavailable or which have been purposely moved to another location. When sufficient full 12 lead ECG complexes have been accumulated for the patient, then the analysis described above with reference to FIG. 1 and FIG. 2 is performed on those complexes, a new entry in the database 110 is created for the patient containing the matrices and associated similarity coefficients resulting from that analysis, and the processing continues as described above using the newly created entry in the database 110 for the patient.

It is also possible to partition the people in the general population discussed above into groups termed categories. For example, groupings may be made by sex, by weight, by age group, by disease and/or by cardiac health (e.g. normal, ischemic/acute myocardial infarction, bundle branch blockage, etc.). The ECG complexes associated with the general population of patients may be partitioned in a corresponding manner and analyzed separately as described above with reference to FIG. 1 and FIG. 2 to produce further category-specific general-population entries in the database 110, designated as GENERAL 2 to GENERAL M in FIG. 1.

When a patient is being prepared for an ECG, the operator manipulates the user controls 314 on the display device 310 to supply characteristics of the patient (name, sex, age, weight, etc.) to the controller 308. As described above, the controller 308 queries the database 110 for a patient entry for that patient. If a patient does not have a patient entry in the database 110, then the other characteristics related to that patient are processed by the controller 308 to assign the patient to one of the available categories. The controller 308 then retrieves the category-specific general population entry corresponding to the category to which the patient was assigned, and uses the synthesis entries in that entry to provide a 12 lead ECG until that patient is assigned his own entry in the database 110.

A special case producing anomalous lead signals occurs when a patient moves. For example, normal ECG monitoring assumes a patient in the supine position. If the patient rolls onto his side, or sits or stands up, then the ECG lead signal characteristics can change, even though there is no clinical change in heart function. For example, the change in body position can produce changes in the ST levels, or in the T wave morphology. This can lead to false alarms, or misinterpretation of the ECG trend data. Techniques are known to detect body position changes based on detection of amplitude variations in the ECG lead signals and/or changes in the cardiac electrical axis. The ECG system illustrated in FIG. 1 and FIG. 4 may be used to detect and compensate for body position changes.

Figure 5:
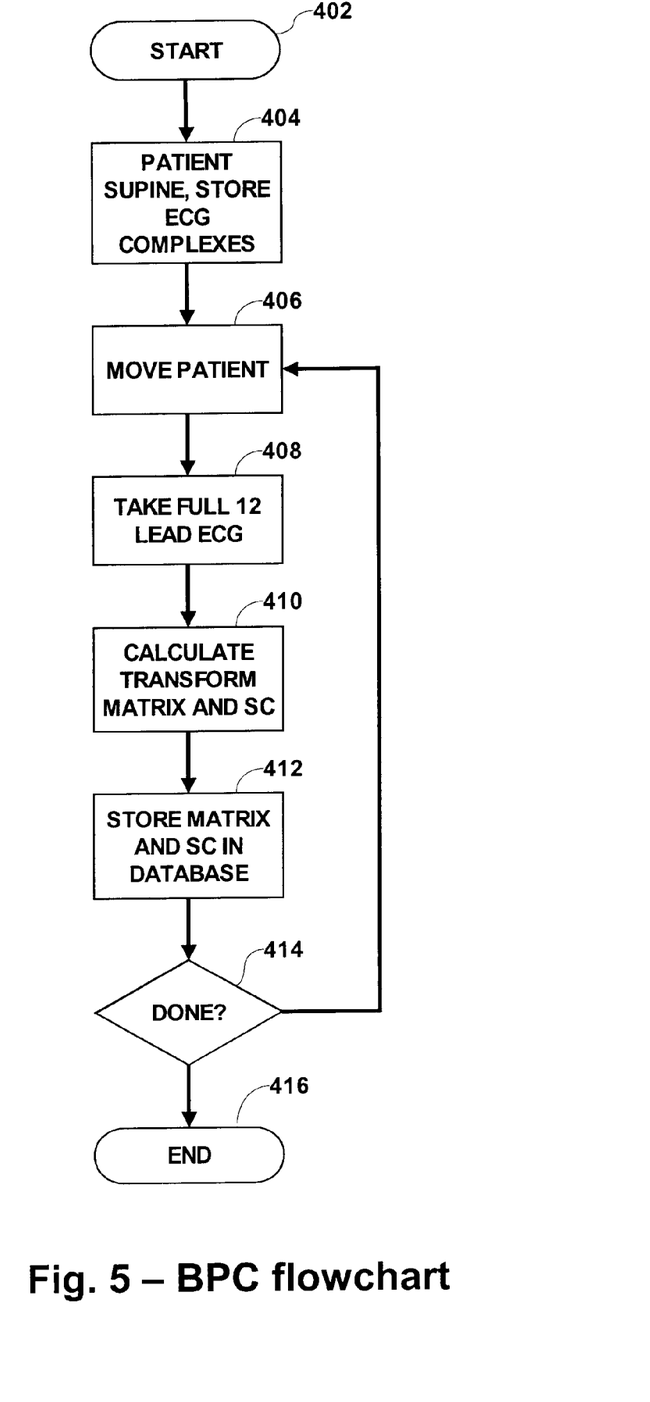
FIG. 5 and FIG. 6 are flowcharts illustrating the operation of the system illustrated in FIG. 1 in response to body position changes.
Figure 6:
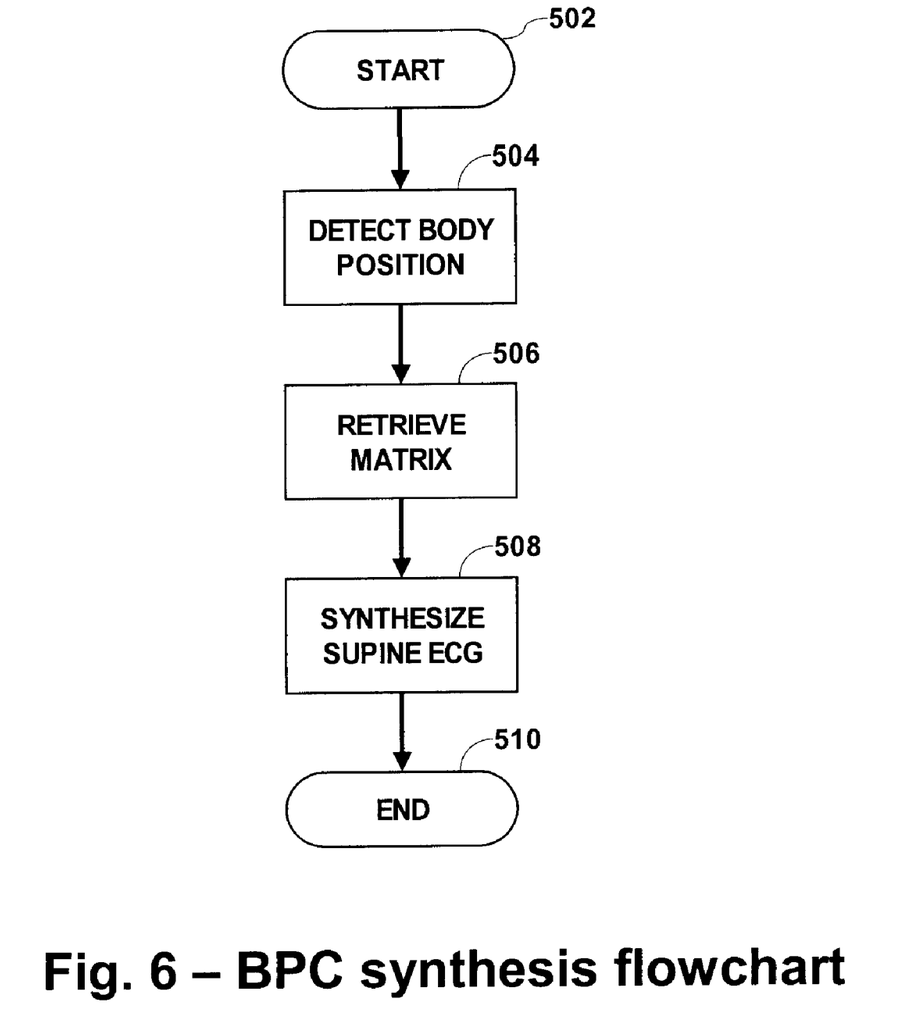

FIG. 5 and FIG. 6 are flowcharts illustrating the operation of the portions of the system illustrated in FIG. 1 and FIG. 4, respectively, in response to patient body position changes. FIG. 5 illustrates the operation of the system illustrated in FIG. 1 in an analysis mode. In the analysis mode, a plurality of matrices is derived, each operating in the manner described above with reference to FIG. 3 to transform ECG lead signals received from a patient in one body position to corresponding synthesized ECG lead signals simulating the patient being in the supine body position. For example, matrices are derived for the patient on his left side, on his right side, right up 60 degrees, standing, etc.

The body position analysis mode begins in block 402. In block 404 the patient is placed in a supine position by the operator. This position is considered the reference position, and all alarms, etc., are based on ECG signals received in this position. A full-12 lead ECG is taken and an ECG complex, possibly aggregated, as described above, is stored in the memory 106. In block 406, the patient is moved to another position, e.g. on the left side. In block 408, a full 12 lead ECG is taken in this body position, and an ECG complex, possibly aggregated, is stored in the memory 106. In block 410, the analyzer 108 retrieves from the memory 106 the ECG complex for the new body position, e.g. left side, and the ECG complex data for the supine body position, in a known manner, and compares them. Using a linear regression analysis, coefficients are derived for a set of linear equations to transform the ECG complex data corresponding to the new body position, e.g. left side, to synthesized ECG complex data approximating the ECG complex data corresponding to the supine position. In a preferred embodiment, the QRST segment is used for the regression analysis. These coefficients form another matrix M. Also in the manner described above, a similarity coefficient SC is derived giving a measure of the accuracy of the transformation. In block 412, the matrix M and the similarity coefficient SC are stored in a further matrix entry in the patient entry (patient 2 in FIG. 1).

In block 414, it is determined if transformation matrices have been derived for all the desired body positions. If so, then the analysis mode ends in block 416. Otherwise, the patient is moved to another position in block 406, and the process of blocks 408 to 412 is repeated for this new position. The result is another group of matrices and similarity coefficients stored in the patent entry in the database 110.

One skilled in the art will understand that, as described above, the same process may be applied to an ECG lead complex aggregated from the general population and the derived matrices and similarity coefficients stored in a general entry (GENERAL 1). Further, also as described above, the same process may be performed on ECG lead complexes aggregated from portions of the general population partitioned according to, e.g. sex, age, weight, etc., and the derived matrices and similarity coefficients stored in the general entry corresponding to that partition (GENERAL 2 to GENERAL M).

FIG. 6 is a flowchart illustrating the operation in a synthesis mode of the portion of the system illustrated in FIG. 4 in response to body position changes. The synthesis mode starts in block 502. In block 504, the position of the body of the patient is detected. The controller 308 retrieves the matrix M and similarity coefficient SC corresponding to the detected body position. The controller 308 inserts the retrieved matrix M into the matrix 307 in the synthesizer 306. In block 508, the synthesizer 306 performs the matrix multiplication described above with reference to FIG. 3 to transform the received ECG lead signals from the preprocessor 104 to synthesized ECG lead signals corresponding to the patient being in the supine position. The synthesized ECG lead signals and associated similarity coefficient are then displayed on the display screen 312 of the display device 310. As described above, an indication that the displayed ECG lead signals are synthesized may also be displayed on the display screen 312. In this manner, any trend data, such as ST-trends, or any alarms, such as ischemia alerts, are properly compensated for changes in patient body position, thus improving accuracy of monitoring and minimizing false alarms.

The analysis and synthesis described above for detecting and compensating for body position changes is based on a scalar approach using linear regression. An alternative approach is a spatial approach. In this approach, instead of synthesizing ECG lead signals transformed to the supine position using coefficients of a set of linear equations, a vector analysis is used. Vectorcardiographic (VCG) signals are derived from the received ECG lead signals by applying an inverse Dower transform, in a known manner. Calculations based on the VCG signals provide axes for the P, QRS and T-waves for the reference supine patient position, and for the different patient body positions. The length and rotation angle from the supine position to the other patient body positions are then calculated. This length and angle data is available for transforming the received VCG signals to synthesized VCG signals corresponding to the reference supine position. This length and angle data may also be used to detect a patient body position change. The synthesized VCG signals may be transformed back to standard 12 lead ECG lead signals by applying an inverse Dower transformation to them.

In a preferred embodiment, body position changes are detected using the spatial approach described above, while the scalar, linear regression, approach is used to transform the received ECG lead signals to the reference supine position. Such an arrangement optimizes the detection of patient body position changes and the accuracy of ST-trend data.

What is claimed is:

1. An electrocardiogram system comprising:
   a source of an ECG lead signal source;
   a database, for storing patient specific data corresponding to the source of the ECG lead signal source;
   a synthesizer, coupled to the ECG lead signal source, for retrieving the patient specific data from said database and generating a synthesized ECG lead signal corresponding to the patient specific data;
   a controller for generating an indication of an anomalous signal if the ECG lead signal is not substantially the same as the synthesized ECG lead signal source.

2. An electrocardiogram system comprising:
   a source of an ECG lead signal source;
   a synthesizer, coupled to the ECG lead signal source, for generating a synthesized ECG lead signal corresponding to the ECG lead signal;
   a controller for generating an indication of an anomalous signal if the ECG lead signal is not substantially the same as the synthesized ECG lead signal source, wherein when an anomalous signal is indicated the controller substitutes the synthesized ECG lead signal for the ECG lead signal.

3. An electrocardiogram system comprising:
   a source of an ECG lead signal source; a synthesizer, coupled to the ECG lead signal source, for generating a synthesized ECG lead signal corresponding to the ECG lead signal;
   a controller for generating an indication of an anomalous signal if the ECG lead signal is not substantially the same as the synthesized ECG lead signal source, wherein
   the controller correlates the synthesized ECG lead signal against the ECG lead signal and generates the indication of an anomalous signal if there is not a strong correlation.

4. An electrocardiogram system comprising:
   a source of an ECG lead signal source;
   a synthesizer, coupled to the ECG lead signal source, for generating a synthesized ECG lead signal corresponding to the ECG lead signal;
   a controller for generating an indication of an anomalous signal if the ECG lead signal is not substantially the same as the synthesized ECG lead signal source, wherein:
   the ECG lead signal source comprises an electrode, intended to be attached to a patient; and
   an indication of an anomalous signal indicates that the electrode is not attached to the patient.

5. An electrocardiogram system comprising:
   a source of an ECG lead signal source;
   a synthesizer, coupled to the ECG lead signal source, for generating a synthesized ECG lead signal corresponding to the ECG lead signal;
   a controller for generating an indication of an anomalous signal if the ECG lead signal is not substantially the same as the synthesized ECG lead signal source, wherein:
   the ECG lead signal source comprises an electrode, intended to be attached to a patient at a predetermined location; and
   an indication of an anomalous signal indicates that the electrode is not attached to the patient at the predetermined location.

6. An electrocardiogram system comprising:
   a source of an ECG lead signal source;
   a synthesizer, coupled to the ECG lead signal source, for generating a synthesized ECG lead signal corresponding to the ECG lead signal;
   a controller for generating an indication of an anomalous signal if the ECG lead signal is not substantially the same as the synthesized ECG lead signal source, wherein:
   the ECG lead signal source comprises a pair of electrodes, intended to be attached to a patient at respective predetermined locations, generating the ECG lead signal;
   the controller correlates the synthesized ECG lead signal against the ECG lead signal; and
   a strong positive correlation indicates that the electrodes are attached to the correct respective predetermined locations and a strong negative correlation indicates that the electrodes are respectively attached to the predetermined location for the other electrode.

7. A electrocardiogram (ECG) system, comprising:
   a source of ECG lead signals;
   a database, comprising a plurality of entries, each entry containing data for translating a 12 lead ECG for a patient in a corresponding body position to a synthesized 12 lead ECG for the patient in a reference body position;
   a body position detector, for detecting the body position of the patient;
   a controller, coupled to the body position detector and the database, and comprising circuitry for:
   receiving information from the body position detector relating to body position of the patient; and
   selecting the entry from the database most closely corresponding to the detected body position of the patient; and
   a synthesizer, coupled to the ECG lead signal source, and the controller, for receiving the translating data in the selected entry, synthesizing a 12 lead ECG for the reference body position from the 12 lead ECG signals from the ECG lead signal source, and supplying data representing the synthesized 12 lead ECG to a user.

8. The electrocardiogram system of claim 7 wherein the database entries comprise entries which are specific to the patient.

9. The electrocardiogram system of claim 7 wherein the database entries comprise entries which are derived from a general patient population.

10. The electrocardiogram system of claim 9 wherein the database entries comprise entries which are derived from portions of the general patient population partitioned according to patient characteristics.

11. The electrocardiogram system of claim 10 wherein the patient characteristics are selected from the group consisting of age, sex, weight, heart condition.

12. The electrocardiogram system of claim 7 further comprising
   a user interface including a display screen capable of displaying graphical information; and
   the controller supplies information to the user indicating the selected configuration in graphical form.

13. The electrocardiogram system of claim 7 wherein the body position detector comprises circuitry for receiving data from the user representing the body position of the patient.

14. The electrocardiogram system of claim 7 wherein the body position detector comprises:
   circuitry for transforming the 12 lead ECG signals from the ECG lead signal source to a vectorcardiogram (VDG) and deriving axes for the P, QRS and T-waves for the body position of the patient;
   deriving the length and rotation of derived axes from those for the patient in the reference position;
   determining the body position of the patient from the length and rotation of the derived axes.

15. An electrocardiogram (ECG) system, comprising:
   a source of ECG lead signals, comprising electrodes intended to be attached to a patient;
   a user interface, for supplying information to and receiving information from a user;
   a database, comprising a plurality of entries, each entry containing data for synthesizing a 12 lead ECG from a subset of leads derived from a number of electrodes attached to the patient in a corresponding configuration and an accuracy measure for the synthesized 12 lead ECG;
   a controller, coupled to the user interface and the database, and comprising circuitry for:
      receiving information from the user interface relating to a number of available electrodes;
      retrieving entries from the database for configurations in which the number of electrodes is the same as the number of available electrodes; and
      selecting the entry having the highest accuracy measure, and supplying information to the user indicating the selected configuration for the available electrodes; and
   a synthesizer, coupled to the ECG lead signal source, the controller, and the user interface, for receiving the synthesizing data in the selected entry, synthesizing a 12 lead ECG from the electrodes attached to the patient in the selected configuration, and supplying data representing the synthesized 12 lead ECG and the accuracy measure to the user interface.

16. The electrocardiogram system of claim 15 wherein non-available electrodes are attached to the patient in non-standard locations and data representing ECG lead signals from these electrodes is supplied to the user interface.

17. The electrocardiogram system of claim 15 wherein the database entries comprise entries which are specific to the patient.

18. The electrocardiogram system of claim 15 wherein the database entries comprise entries which are derived from a general patient population.

19. The electrocardiogram system of claim 18 wherein the database entries comprise entries which are derived from portions of the general patient population partitioned according to patient characteristics.

20. The electrocardiogram system of claim 19 wherein the patient characteristics are selected from the group consisting of age, sex, weight, heart condition.

21. The electrocardiogram system of claim 15 wherein:
   the user interface comprises a display screen capable of displaying graphical information; and
   the controller supplies information to the user indicating the selected configuration in graphical form.

22. An electrocardiogram (ECG) system, comprising:
   a source of ECG lead signals, comprising electrodes intended to be attached to a patient;
   a user interface, for supplying information to and receiving information from a user;
   a database, comprising a plurality of entries, each entry containing patient specific data for synthesizing a 12 lead ECG from a subset of leads derived from a number of electrodes attached to the patient in a corresponding configuration and an accuracy measure for the synthesized 12 lead ECG;
   a controller, coupled to the user interface and the database, and comprising circuitry for;
      receiving information from the user interface relating to a number of available electrodes;
      retrieving entries from the database for configurations in which the number of electrodes is the same as the number of available electrodes;
      supplying data representing the retrieved entries, including the respective accuracy measures, to the user interface;
      receiving data from the user interface representing a selected one of the retrieved entries; and
   a synthesizer, coupled to the ECG lead signal source, the controller, and the user interface, for receiving the patient specific synthesizing data in the selected entry, synthesizing a 12 lead ECG from the electrodes attached to the patient in the selected configuration, and supplying data representing the synthesized 12 lead. ECG and the accuracy measure to the user interface.

23. The electrocardiogram system of claim 22 wherein non-available electrodes are attached to the patient in non-standard locations and data representing ECG lead signals from these electrodes is supplied to the user interface.

24. The electrocardiogram system of claim 22 wherein the database entries comprise entries which are specific to the patient.

25. The electrocardiogram system of claim 22 wherein the database entries comprise entries which are derived from a general patient population.

26. The electrocardiogram system of claim 25 wherein the database entries comprise entries which are derived from portions of the general patient population partitioned according to patient characteristics.

27. The electrocardiogram system of claim 26 wherein the patient characteristics are selected from the group consisting of age, sex, weight, heart condition.

28. The electrocardiogram system of claim 22 wherein:
   the user interface comprises a display screen capable of displaying graphical information; and
   the controller supplies information to the user indicating the selected configuration in graphical form.

29. The electrocardiogram system of claim 22 wherein:
   the user interface comprises a display screen capable of displaying graphical information; and the controller, after receiving data from the user interface supplies information to the user indicating the selected configuration in graphical form.

30. A method for operating an electrocardiogram (ECG) system, comprising the steps of:

detecting the body position of a patient;

retrieving from a database, an entry containing translation data for synthesizing a 12 lead ECG for a reference body position from a 12 lead ECG at a body position closest to the detected body position;

receiving a 12 lead ECG from the patient;

synthesizing a 12 lead ECG for the reference body position from the received 12 lead ECG.

31. A method for operating an electrocardiogram (ECG) system, comprising the steps of:

requesting information from a user representing a number of available electrodes;

retrieving from a database respective entries, each entry containing data for synthesizing a 12 lead ECG from the number available electrodes and an accuracy measure;

selecting the entry having the highest accuracy measure;

synthesizing a 12 lead ECG from the available electrodes in response to the synthesizing data in the selected entry; and displaying the synthesized 12 lead ECG and the accuracy measure.

32. The method of claim 31 wherein:

the information requesting step further comprises the step of requesting information from the user representing electrode locations on the patient which are unavailable;

the retrieving step further comprises the step of retrieving entries from the database for the number of available electrodes at available locations on the patient.

33. A method for operating an electrocardiogram (ECG) system, comprising the steps of;

requesting information from a user representing a number of available electrodes;

retrieving from a database respective entries, each entry containing patient specific data for synthesizing a 12 lead ECG from the number available electrodes and an accuracy measure;

displaying for a user information representing the retrieved entries, including the accuracy measure;

selecting by the user one of the displayed entries;

synthesizing a 12 lead ECG from the available electrodes in response to the patient specific synthesizing data in the selected entry; and displaying the synthesized 12 lead ECG and the accuracy measure.

* * * * *